United States Patent [19]
Kyomori et al.
[11] 3,969,408
[45] July 13, 1976

[54] 2-ALKYL-5-OXIMINOCYCLOPENTANONE AND THE METHOD OF PREPARING THE SAME

[75] Inventors: Hiroyuki Kyomori, Yachiyo; Kazuhiro Sasaki, Fuchu; Mitsuhiro Takahashi, Tokyo, all of Japan

[73] Assignee: Kobayashi Perfumery Co., Ltd., Tokyo, Japan

[22] Filed: Dec. 18, 1974

[21] Appl. No.: 533,792

[30] Foreign Application Priority Data

Mar. 5, 1974 Japan ............................... 49-25518

[52] U.S. Cl. ......................... 260/566 A; 260/586 R
[51] Int. Cl.$^2$ ....................................... C07C 131/02
[58] Field of Search ................................. 260/566 A

[56] References Cited

OTHER PUBLICATIONS

Smissman et al., J. Org. Chem., vol. 27, pp. 2316–2318 (1962).

*Primary Examiner*—Gerald A. Schwartz
*Attorney, Agent, or Firm*—Kemon, Palmer & Estabrook

[57] ABSTRACT

2-alkyl-5-oximinocyclopentanone useful as the raw material of perfume and other chemicals, the chemical structure of which may be expressed by the general formula:

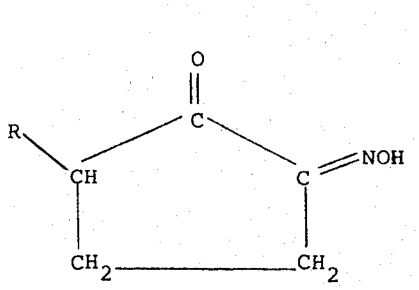

where R is a lower alkyl group, and the method of preparing the same.

5 Claims, 4 Drawing Figures

2-ALKYL-5-OXIMINOCYCLOPENTANONE AND THE METHOD OF PREPARING THE SAME

BACKGROUND OF THE INVENTION

This invention relates to a novel compound of 2-alkyl-5-oximinocyclopentanone useful as the raw material of perfume and other chemicals.

2-hydroxy-3-alkyl-2-cyclopenten-1-one itself is very important as perfume, particularly, food perfume. As the result of the recent development of the food industry, increasing demand is made for this compound. Further, the way is being paved to prepare other perfumes and chemicals using the above-mentioned compound as a starting material.

The known processes of synthesizing said compound include (A) the process of using esters of propionic acid and esters of oxalic acid as the raw material (refer to "Nippon Nogei Kagaku Kaishi", Vol. 44, p. 46, 1970) and (B) the process of using esters of adipic acid as the raw material (refer to the Japanese Patent Application Publications Nos. 14,989/66, 17,180/68, 6817/69, 10,493/70 and West German Patent Application Disclosure No. 2,005,160). However, close study has shown that the above-mentioned processes are still accompanied with drawbacks in that the processes have a low yield, and involve long and complicated reaction steps. Therefore, strong demand has been made for the development of technology capable of resolving these difficulties.

SUMMARY OF THE INVENTION

It is accordingly the object of this invention to provide a novel compound which the present inventors have synthesized for the first time in connection with the development of an industrially advantageous method of preparing the aforesaid 2-hydroxy-3-alkyl-2-cyclopenten-1-one, namely, 2-alkyl-5-oximinocyclopentanone whose chemical structure may be expressed by the general formula:

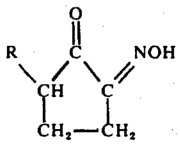

(I)

where R is a lower alkyl group, generally methyl group, ethyl group, propyl group and butyl group. The above-mentioned compound 2-alkyl-5-oximinocyclopentanone (I) is very important as a starting material in advantageously preparing the aforesaid 2-hydroxy-3-alkyl-2-cyclopenten-1-one useful, for example, as perfume, the chemical structure of which may be expressed by the general formula:

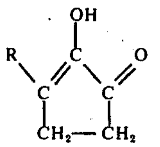

(II)

where R is a lower alkyl group, generally methyl group, ethyl group, propyl group and butyl group and also as the raw material of other chemicals.

The above-mentioned 2-alkyl-5-oximinocyclopentanone (I) can be prepared by reacting 2-alkyl-5-carboalkoxycyclopentanone whose chemical structure may be expressed by the general formula:

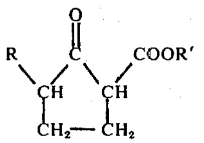

(III)

where R and R′ are lower alkyl groups with nitrites in the presence of water and alkali, and thereafter rendering the resultant reaction liquid acidic.

DETAILED DESCRIPTION OF THE INVENTION

Figure 1:
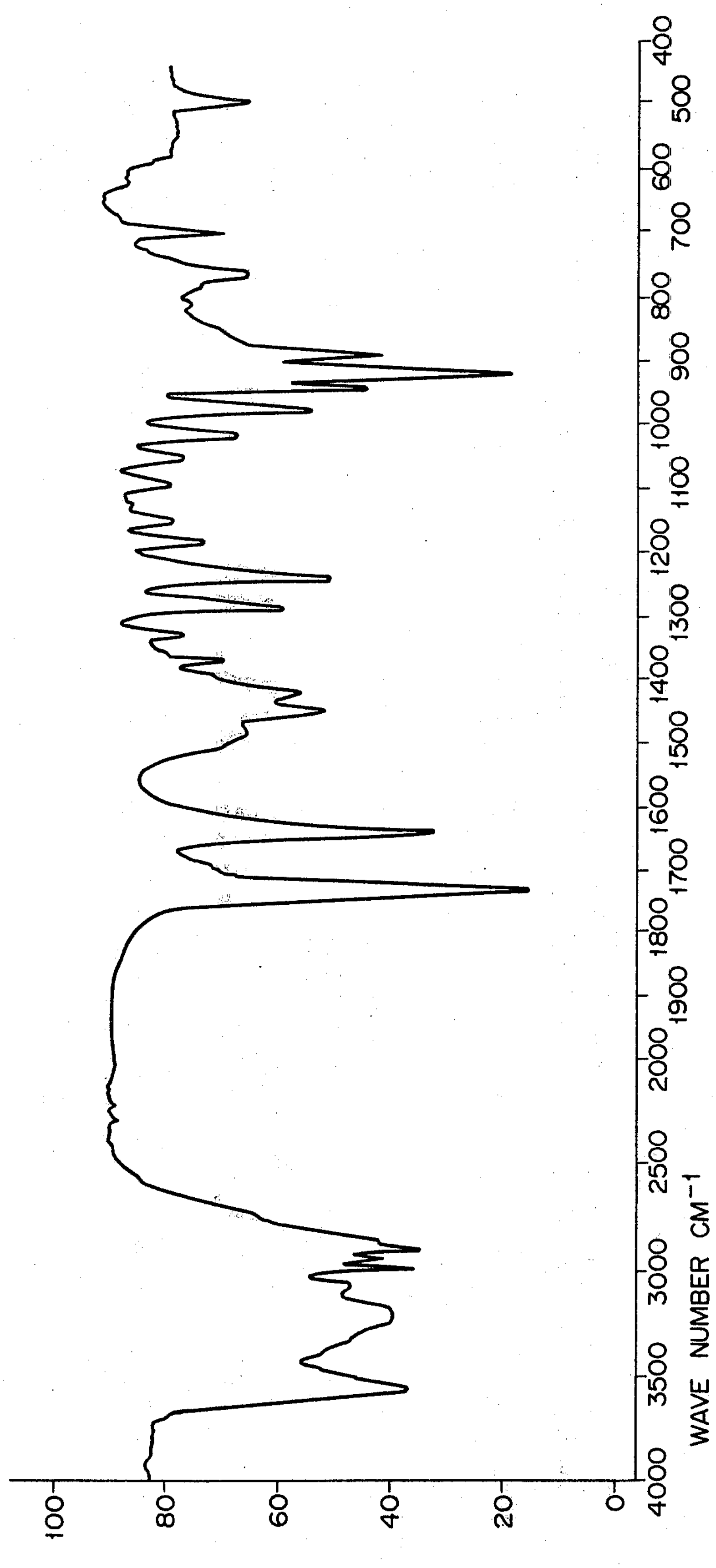
FIGS. 1, 2 and 3 are the infrared absorption spectra of the compounds obtained in Examples 1, 2 and 3 of this invention.

While earnestly studying an industrially advantageous process of synthesizing 2-hydroxy-3-alkyl-2-cyclopenten-1-one whose chemical structure is expressed by the above general formula (II), the present inventors succeeded in synthesizing 2-alkyl-5-oximinocyclopentanone, a novel compound whose chemical structure is expressed by the above general formula (I). It has been disclosed that this novel compound is an industrially very important raw material in preparing 2-hydroxy-3-alkyl-2-cyclopenten-1-one (II).

The 2-alkyl-5-oximinocyclopentanone (I) of this invention can be synthesized in good yield by reacting the starting material of the aforesaid 2-alkyl-5-carboalkoxycyclopentanone (III) with nitrites in the presence of water and alkali and thereafter rendering the resultant reaction liquid acidic.

For preparation of the desired 2-alkyl-5-oximinocyclopentanone (I) from 2-alkyl-5-carboalkoxycyclopentanone (III), it is necessary, as naturally expected, to activate a carbon atom occupying the fifth position of the chemical structure of the raw 2-alkyl-5-carboalkoxycyclopentanone (III) for nitrosation and hydrolyze and decarboxylate the carboalkoxy group assuming the fifth position. As the result of studies, the present inventors have found that though reaction between 2-alkyl-5-carboalkoxycyclopentanone (III) and nitrites is not smoothly effected under a neutral or acid condition, yet the aforesaid nitrosation and hydrolysis are very smoothly carried out in the presence of water and alkali and that when the reaction liquid is rendered acidic after completion of reaction, then decarboxylation and prototropy take place to precipitate the desired 2-alkyl-5-oximinocyclopentanone (I).

2-alkyl-5-carboalkoxycyclopentanone (III) used as a starting material in the method of this invention can be easily prepared by the known processes, for example, those set forth in "Journal of Organic Chemistry", 29, 2781 (1964) by K. Sisido et al and also in said Journal, 30, 183 (1965) by W. L. Meyer et al.

Referring to the general formula (III), R and R′ generally denote methyl group, ethyl group, propyl group and butyl group. Nitrites used in nitrosation are not subject to any particular limitation, provided they can be applied as ordinary nitrosating agents. However, particularly preferred are potassium nitrite and sodium nitrite. Proportion of nitrites is chosen to be preferably 1 to 3 mols per mol of the raw 2-alkyl-5-carboalkoxycyclopentanone (III), or more preferably 1 to 1.1 mols. The alkalis used in this invention include sodium hydroxide, potassium hydroxide, sodium carbonate and potassium carbonate. Particularly preferred among these alkalis are sodium hydroxide and potassium hydroxide. Proportion of alkali is chosen to be preferably 1 to 3 mols, more preferably 1 to 1.5 mols and most preferably 1 to 1.2 mols per mol of the raw 2-alkyl-5-carboalkoxycyclopentanone (III).

As mentioned above, the above-mentioned reaction is carried out in the presence of water. In this case, the total amount of water used is chosen to be preferably 200 to 2000 ml per mol of the raw 2-alkyl-5-carboalkoxycyclopentanone (III), or more preferably 300 to 1200 ml. While solid nitrite and alkali and water may be separately added to the reaction system, it is convenient to add the nitrite and alkali in the form of a water solution.

Reaction temperature is generally chosen to range between 0° and 60°C, preferably between 10° and 40°C, though varying with the kind of nitrite and alkali used as well as with the number of carbon atoms contained in the R and R' groups of the raw 2-alkyl-5-carboalkoxycyclopentanone (III). Reaction time is generally chosen to be 1 to 60 hours, though varying with the number of carbon atoms contained in said R and R' groups as well as with reaction temperature.

Hydrochloric acid or sulfuric acid, for example, is adapted to be used in rendering the reaction liquid acidic for decarboxylation and prototropy after nitrosation and hydrolysis of the carboalkoxy group. When rendered acidic, the reaction system is generally chosen to be set at a lower level than room temperature, preferably a lower level than 5°C. Proportion of acid is chosen to be preferably 2 to 6 equivalents per mol of the raw 2-alkyl-5-carboalkoxycyclopentanone (III), or more preferably 2 to 2.3 equivalents.

In synthesis of 2-alkyl-5-oximinopentanone, an aqueous solution of a prescribed amount of alkali is normally added to 2-alkyl-5-carboalkoxycyclopentanone (III) as the first step. Addition of an aqueous solution of alkali results in precipitation of white crystals. Various studies have shown said white crystals to be alkali metal (like sodium and potassium) salt of 2-alkyl-5-carboalkoxycyclopentanone (III). These white crystals indicate an infrared spectrum (FIG. 4) which completely coincides with that of alkali metal salt of the 2-alkyl-5-carboalkoxycyclopentanone obtained by a process which omits neutralization of the catalyst alkali with acid from the process of K. Sisido et al (disclosed in the "Journal of Organic Chemistry", 27, 2781, 1964) which consists in isomerizing 2-alkyl-2-carboalkoxycyclopentanone with alkali alcoholate into 2-alkyl-5-carboalkoxycyclopentanone. Where the alkali metal salt of 2-alkyl-5-carboalkoxycyclopentanone thus obtained is substituted for 2-alkyl-5-carboalkoxycyclopentanone as a starting material in a state suspended in water and, if necessary, mixed with a small amount of alkali and with nitrite and further with acid to render the reaction liquid acidic, then the desired 2-alkyl-5-oximinocyclopentanone (I) can be produced in as good yield as in the above-mentioned case.

When the 2-alkyl-5-oximinocyclopentanone (I) is subjected to nitrosation and hydrolysis, these reactions may be effected in the presence of solvents such as methanol, ethanol, dioxane or tetrahydrofuran, insofar as said nitrosation and hydrolysis are not obstructed.

As mentioned above, the 2-alkyl-5-oximinocyclopentanone (I) of this invention can be prepared by a very simple process and in high yield. This compound (I) can be made merely by hydrolysis into 2-hydroxy-3-alkyl-2-cyclopenten-1-one (II). Therefore, the subject compound (I) is important as the raw material of not only perfume but also other chemicals.

This invention will be more fully understood by reference to the examples which follow.

EXAMPLE 1

A solution prepared by dissolving 2.2g of sodium hydroxide in 20 ml of water was dripped at a lower temperature than 20°C into 7.8g of 2-methyl-5-carbomethoxycyclopentanone. A solution prepared by dissolving 3.44g of sodium nitrite in 10 ml of water was further added to the reaction system. The mass was stirred 3 hours at 40°C and then cooled to a lower temperature than 5°C. Upon addition of 18.3 ml of 6N hydrochloric acid, crystals were immediately precipitated. Upon washing the crystals with a small amount of cold water after filtration, 4.8g (76% yield) of white crystals of the desired 2-methyl-5-oximinocyclopentanone were obtained. The white crystals displayed the following physiochemical properties:

| | | |
|---|---|---|
| Melting point : 51 to 53°C (corrected) | | |
| Nuclear magnetic resonance (NMR) : (CDCl$_3$ solution, ppm) | | 1.18 (3H, d)<br>1.3 to 1.9 (1H, m)<br>2.1 to 3.3 (4H, m)<br>8.65 (1H, s) |
| Infrared absorption (IR) : As shown in FIG. 1 (KBr tablet) | | |
| Analysis of elements : | C 56.30%<br>H 7.05% | |
| | C 56.88%<br>H 7.14% | as calculated from $C_6H_9NO_2$ |

EXAMPLE 2

A solution prepared by dissolving 1.47g of sodium hydroxide in 28 ml of water was dripped at a lower temperature than 20°C into 5.7g of 2-ethyl-5carbomethoxycyclopentanone. A solution prepared by dissolving 2.3g of sodium nitrite in 7 ml of water was further added to the reaction system. The mass was stirred 24 hours at 40°C, and then cooled to a lower temperature than 5°C. Upon addition of 14.7 ml of 6N hydrochloric acid, crystals were immediately precipitated. Upon washing the crystals with a small amount of cold water after filtration, 3.4g (72% yield) of white crystals of the object 2-ethyl-5-oximinocyclopentanone were obtained. The white crystals indicated the following physiochemical properties.

Figure 2:
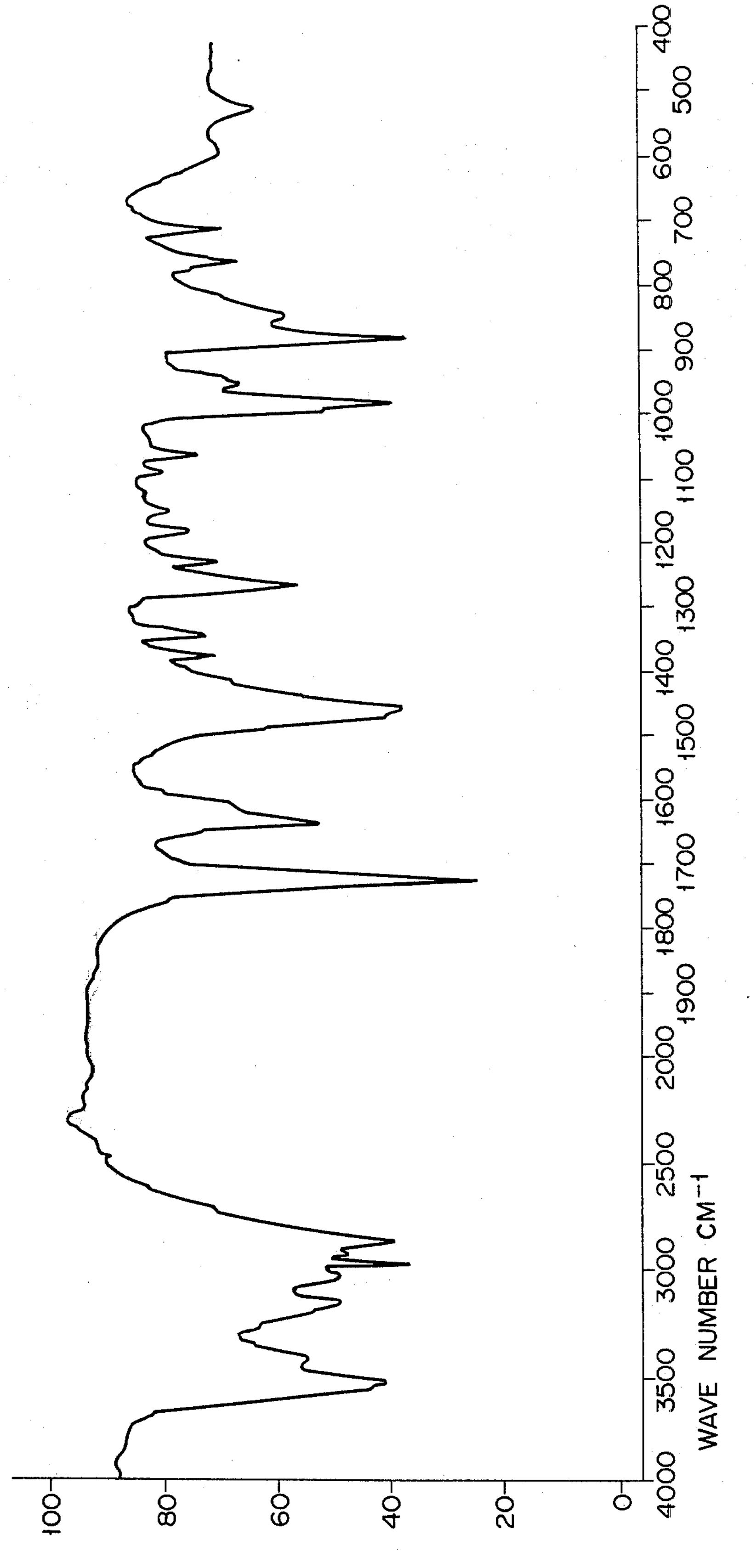

| | | |
|---|---|---|
| Melting point : 41 to 40°C (corrected) | | |
| NMR (CDCl$_3$ solution, ppm) : | | 0.95 (3H, t)<br>1.2 to 1.9 (3H, m)<br>1.9 to 3.2 (4H, m)<br>9.4 (1H, s) |
| IR (KBr tablet) : As shown in FIG. 2 | | |
| Analysis of elements : | C 59.21%<br>H 7.61% | |
| | C 59.56%<br>H 7.85% | as calculated from $C_7H_{11}NO_2$ |

EXAMPLE 3

Figure 3:
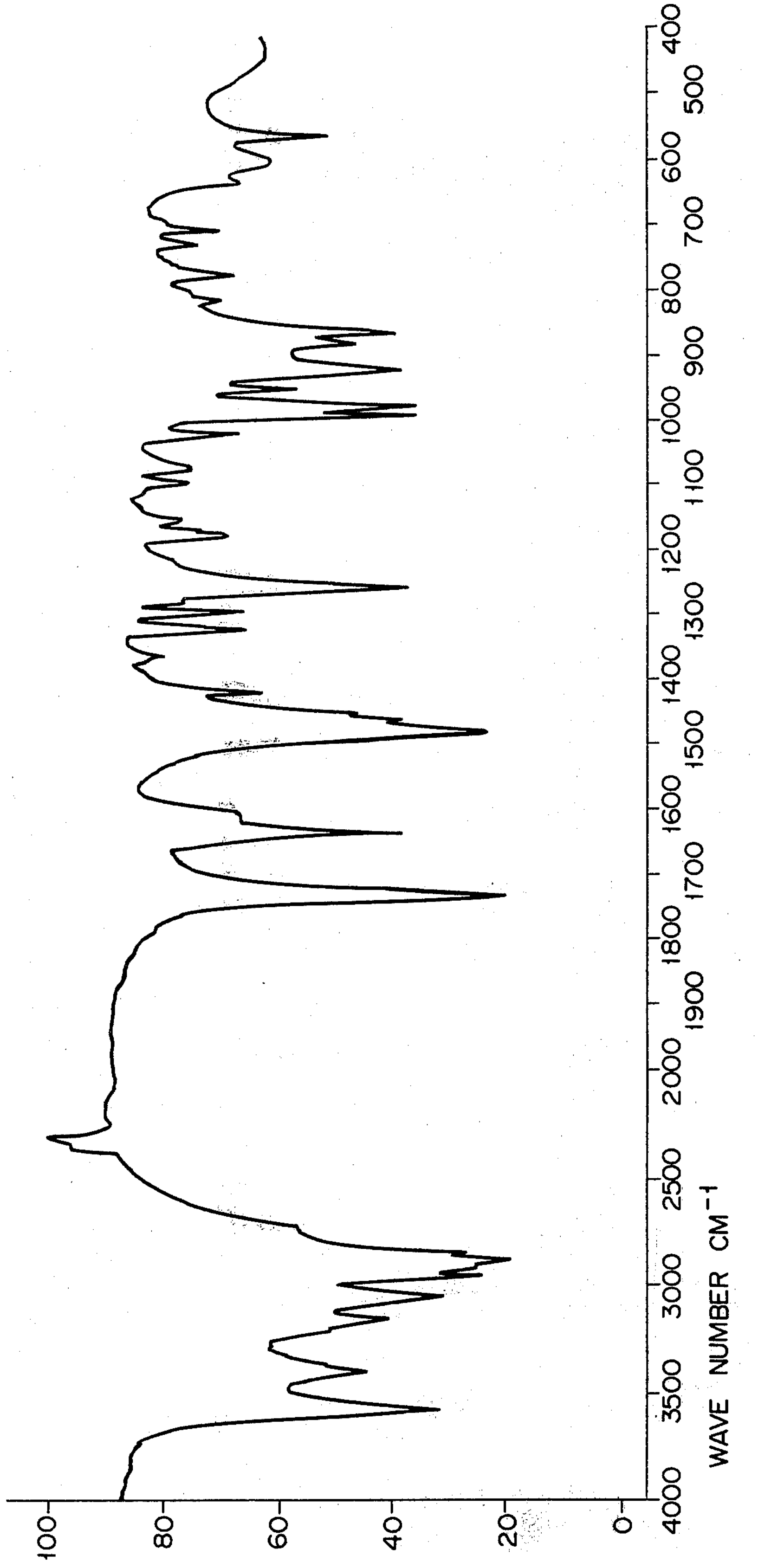

A solution prepared by dissolving 1.47g of sodium hydroxide in 28 ml of water was dripped at a lower temperature than 20°C into 6.13g of 2-n-propyl-5-carbomethoxycyclopentanone. A solution prepared by dissolving 2.3g of sodium nitrite in 7 ml of water was further added to the reaction system. The mass was stirred 6 hours at 40°C and then cooled to a lower temperature than 5°C. Upon addition of 14.7 ml of 6N hydrochloric acid, crystals were immediately precipitated. Upon washing the crystals with a small amount of cold water after filtration, 3.6g (70% yield) of white crystals of the object 2-n-propyl-5-oximinocyclopentanone were obtained. The white crystals showed the following physiochemical properties:

| | | |
|---|---|---|
| Melting point : 55 to 57°C (corrected) | | |
| NMR ($CDCl_3$ solution, ppm) : | 0.92 (3H, t) | |
| | 1.1 to 2.0 (5H, m) | |
| | 2.0 to 3.2 (4H, m) | |
| | 8.9 (1H, s) | |
| IR (KBr tablet) : As shown in FIG. 3. | | |
| Analysis of elements : | C 61.75% | |
| | H 8.50% | |
| | C 61.92% | as calculated from |
| | H 8.44% | $C_8H_{13}NO_2$ |

EXAMPLE 4

A solution prepared by dissolving 1.47g of sodium hydroxide in 28 ml of water was dripped at a lower temperature than 20°C into 5.7g of 2-methyl-5-carbethoxycyclopentanone. A solution prepared by dissolving 2.3g of sodium nitrite in 7 ml of water was further added to the reaction system. The mass was stirred 3 hours at 40°C and then cooled to a lower temperature than 5°C. Upon addition of 14.7 ml of 6N hydrochloric acid, crystals were immediately precipitated. Upon washing the crystals with a small amount of cold water after filtration, 3.2g (75% yield) of white crystals of the desired 2-methyl-5-oximinocyclopentanone were obtained. The white crystals indicated the same physicochemical properties as in Example 1.

EXAMPLE 5

A solution prepared by dissolving 1.47g of sodium hydroxide in 28 ml of water was dripped at a lower temperature than 20°C into 5.2g of 2-methyl-5-carbomethoxycyclopentanone. A solution prepared by dissolving 3.0g of potassium nitrite in 7 ml of water was further added to the reaction system. The following operation was carried out in the same manner as in Example 4, providing 3.2g (75% yield) of white crystals of the object 2-methyl-5-oximinocyclopentanone. The white crystals indicated the same physicochemical properties as in Example 1.

EXAMPLE 6

A solution prepared by dissolving 2.1g of potassium hydroxide in 28 ml of water was dripped at a lower temperature than 20°C into 5.2g of 2-methyl-5-carbomethoxycyclopentanone. The following operation was effected in the same manner as in Example 4, providing 3.1g (73% yield) of white crystals of the desired 2-methyl-5-oximinocyclopentanone. The white crystals presented the same physicochemical properties as in Example 1.

EXAMPLE 7

A solution prepared by dissolving 1.47g of sodium hydroxide in 28 ml of water was dripped at a lower temperature than 20°C into 5.2g of 2-methyl-5-carbomethoxycyclopentanone. A solution prepared by dissolving 2.3g of sodium nitrite in 7 ml of water was further added to the reaction system. The mass was stirred 3 hours at 40°C, and then cooled to a lower temperature than 5°C, followed by addition of 14.7 ml of 6N sulfuric acid. The following operation was performed in the same manner as in Example 4, obtaining 3.1g (73% yield) of white crystals of the desired 2-methyl-5-oximinocyclopentanone. The white crystals displayed the same physicochemical properties as in Example 1.

EXAMPLE 8

A solution prepared by dissolving 1.47g of sodium hydroxide in 28 ml of water was dripped at a lower temperature than 20°C into 6.13g of 2-methyl-5-carbo-n-propoxycyclopentanone. A solution prepared by dissolving 2.3g of sodium nitrite in 7 ml of water was further added to the reaction system. The mass was stirred 4 hours at 40°C and cooled to a lower temperature than 5°C, followed by addition of 14.7 ml of 6N hydrochloric acid. The following operation was conducted in the same manner as in Example 4, providing 2.9g (68% yield) of white crystals of 2-methyl-5-oximinocyclopentanone. The white crystals indicated the same physicochemical properties as in Example 1.

EXAMPLE 9

Figure 4:
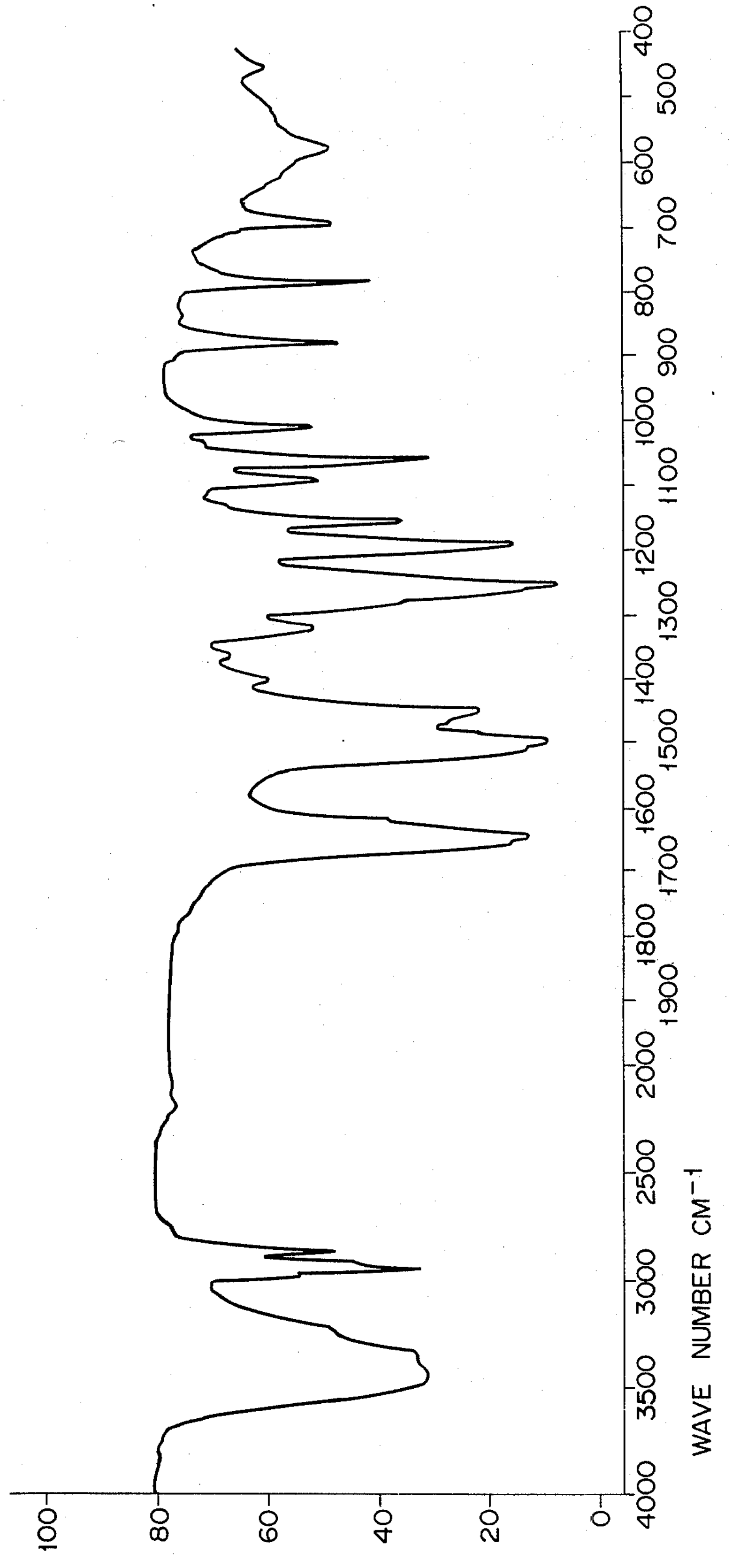
FIG. 4 is the infrared absorption spectrum of the sodium salt of 2-methyl-5-carbomethoxycyclopentanone used in Example 9 of the invention.

A solution prepared by dissolving 1.47g of sodium hydroxide in 28 ml of water was dripped at a lower temperature than 20°C into 5.2g of 2-methyl-5-carbomethoxycyclopentanone. The white crystals which were immediately precipitated were filtered and washed with a small amount of ether, followed by drying. Then white crystals of sodium salt of 2-methyl-5-carbomethoxycyclopentanone were quantitatively obtained. The latter white crystals displayed an infrared spectrum (KBr tablet) as shown in FIG. 4.

When 2.49g of white crystals of sodium salt of 2-methyl-5-carbomethoxycyclopentanone were suspended in cold water and rendered acidic by adding dilute hydrochloric acid, then the mass was separated into an oil layer and a water layer. The water layer thus separated was twice subjected to extraction with 30 ml of ether. A mixture of the oil layer and ether-extract was washed first with 5 ml of saturated aqueous solution of sodium bicarbonate and then twice with 10 ml of water. The mass was dried with anhydrous sodium sulfate and the solvent was recovered under vacuum, quantitatively producing colorless oily crude 2-methyl-5-carbomethoxycyclopentanone. This product presented exactly the same infrared spectrum (liquid film) as that of the initial raw 2-methyl-5-carbomethoxycyclopentanone.

When 2-methyl-2-carbomethoxycyclopentanone was isomerized into 2-methyl-5-carbomethoxycyclopentanone in accordance with the process proposed by K. Sisido et al in the "Journal of Organic Chemistry", 29, 2781, 1964 (cf. the article by W. L. Meyer et al given in the "Journal of Organic Chemistry", 30, 183, 1965) and the resultant reaction liquid was cooled without neutralizing the catalyst of sodium in the last step, then sodium salt of 2-methyl-5-carbomethoxycyclopentanone was produced in higher yield than 80%. Said sodium salt showed the exactly the same infrared spectrum (KBr tablet) as that of the previously mentioned crystals of sodium salt of 2-methyl-5-carbomethoxycyclopentanone obtained by treating 2-methyl-5-carbomethoxycyclopentanone with an aqueous solution of sodium hydroxide.

A solution prepared by dissolving 0.2g of sodium hydroxide in 40 ml of water was dripped at a lower temperature than 20°C into 8.9g of sodium salt of 2-methyl-5-carbomethoxycyclopentanone obtained in the above-mentioned manner. A solution prepared by dissolving 3.4g of sodium nitrite in 10 ml of water was further added to the reaction system. The mass was stirred 6 hours at room temperature and then cooled to a lower temperature than 5°C, followed by addition of 18.3 ml of 6N hydrochloric acid. The following operations were carried out in the same manner as in Example 1, providing 4.7g (74% yield) of white crystals of the desired 2-methyl-5-oximinocyclopentanone. The white crystals displayed the same physicochemical properties as in Example 1.

What we claim is:

1. 2-alkyl-5-oximinocyclopentanone useful as perfume raw material, the chemical structure of which may be expressed by the general formula:

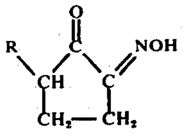

where R is a lower alkyl group.

2. 2-alkyl-5-oximinocyclopentanone according to claim 1, wherein the lower alkyl group denoted by R is a methyl group.

3. 2-alkyl-5-oximinocyclopentanone according to claim 1, wherein the lower alkyl group denoted by R is an ethyl group.

4. 2-alkyl-5-oximinocyclopentanone according to claim 1, wherein the lower alkyl group indicated by R is a propyl group.

5. 2-alkyl-5-oximinocyclopentanone according to claim 1, wherein the lower alkyl group represented by R is a butyl group.

* * * * *